(12) United States Patent
Nicolaescu et al.

(10) Patent No.: US 11,134,975 B2
(45) Date of Patent: Oct. 5, 2021

(54) APPARATUS AND METHOD TO CONTROL OPERATION OF SURGICAL INSTRUMENT BASED ON AUDIBLE FEEDBACK

(71) Applicant: ETHICON LLC, Guaynabo, PR (US)

(72) Inventors: Ion V. Nicolaescu, Carpentersville, IL (US); David C. Yates, West Chester, OH (US)

(73) Assignee: Cilag GmbH International, Zug (CH)

( * ) Notice: Subject to any disclaimer, the term of this patent is extended or adjusted under 35 U.S.C. 154(b) by 787 days.

(21) Appl. No.: 15/692,310

(22) Filed: Aug. 31, 2017

(65) Prior Publication Data
US 2019/0059928 A1    Feb. 28, 2019

(51) Int. Cl.
*A61B 18/14* (2006.01)
*A61B 17/32* (2006.01)
*A61B 18/12* (2006.01)
*A61B 17/00* (2006.01)
*A61B 18/00* (2006.01)

(52) U.S. Cl.
CPC ............... *A61B 17/320068* (2013.01); *A61B 17/320092* (2013.01); *A61B 18/1445* (2013.01); *A61B 18/1206* (2013.01); *A61B 2017/00022* (2013.01); *A61B 2017/00026* (2013.01); *A61B 2017/00106* (2013.01); *A61B 2017/320071* (2017.08); *A61B 2017/320073* (2017.08); *A61B 2017/320082* (2017.08); *A61B 2017/320094* (2017.08); *A61B 2018/0088* (2013.01)

(58) Field of Classification Search
CPC ........ A61B 17/320068; A61B 18/1206; A61B 18/1442; A61B 18/1445; A61B 2017/320073; A61B 2017/320082; A61B 2017/320071
See application file for complete search history.

(56) References Cited

U.S. PATENT DOCUMENTS

| | | | |
|---|---|---|---|
| 5,322,055 A | 6/1994 | Davison et al. |
| 5,792,135 A | 8/1998 | Madhani et al. |
| 5,817,084 A | 10/1998 | Jensen |
| 5,873,873 A | 2/1999 | Smith et al. |
| 5,878,193 A | 3/1999 | Wang et al. |
| 5,980,510 A | 11/1999 | Tsonton et al. |
| 6,231,565 B1 | 5/2001 | Tovey et al. |

(Continued)

OTHER PUBLICATIONS

U.S. Appl. No. 62/509,336, entitled "Control Algorithm for Surgical Instrument with Ultrasonic and Electrosurgical Modalities," filed May 22, 2017.

(Continued)

*Primary Examiner* — Michael F Peffley
*Assistant Examiner* — Bo Ouyang
(74) *Attorney, Agent, or Firm* — Frost Brown Todd LLC

(57) ABSTRACT

An apparatus includes a body, a shaft assembly, an end effector, a first acoustic sensor, and a processor. The shaft assembly extends distally from the body. The end effector is located at the distal end of the shaft assembly. The end effector is operable to apply energy to tissue and thereby change a state of the tissue. The first acoustic sensor is configured to pick up sound emitted by tissue. The processor is in communication with the first acoustic sensor. The processor is configured to provide an automated response in response to a signal from the first acoustic sensor indicating a change in the state of the tissue.

20 Claims, 9 Drawing Sheets

(56) References Cited

U.S. PATENT DOCUMENTS

| | | |
|---|---|---|
| 6,283,981 B1 | 9/2001 | Beaupre |
| 6,309,400 B2 | 10/2001 | Beaupre |
| 6,325,811 B1 | 12/2001 | Messerly |
| 6,364,888 B1 | 4/2002 | Niemeyer |
| 6,423,082 B1 | 7/2002 | Houser et al. |
| 6,500,176 B1 | 12/2002 | Truckai et al. |
| 6,773,444 B2 | 8/2004 | Messerly |
| 6,783,524 B2 | 8/2004 | Anderson |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,524,320 B2 | 4/2009 | Tierney et al. |
| 7,691,098 B2 | 4/2010 | Wallace et al. |
| 7,806,891 B2 | 10/2010 | Nowlin et al. |
| 8,057,498 B2 | 11/2011 | Robertson |
| 8,461,744 B2 | 6/2013 | Wiener et al. |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,939,974 B2 | 1/2015 | Boudreaux et al. |
| 9,089,327 B2 | 7/2015 | Worrell et al. |
| 9,161,803 B2 | 10/2015 | Yates et al. |
| 9,301,759 B2 | 4/2016 | Spivey et al. |
| 9,402,682 B2 | 8/2016 | Worrell et al. |
| 9,545,253 B2 | 1/2017 | Worrell et al. |
| 9,572,622 B2 | 2/2017 | Shelton, IV et al. |
| 2005/0261673 A1* | 11/2005 | Bonner ............... A61B 18/1485 606/41 |
| 2007/0179482 A1* | 8/2007 | Anderson ............ A61B 18/203 606/9 |
| 2008/0177258 A1* | 7/2008 | Govari ............... A61B 18/1492 606/41 |
| 2011/0087212 A1 | 4/2011 | Aldridge et al. |
| 2012/0078139 A1* | 3/2012 | Aldridge ............ A61B 18/1206 601/2 |
| 2012/0078243 A1 | 3/2012 | Worrell et al. |
| 2012/0310115 A1* | 12/2012 | Bedingham ............... A61B 7/04 600/586 |
| 2013/0197363 A1* | 8/2013 | Rankin ............... A61B 18/1492 600/439 |
| 2013/0204241 A1* | 8/2013 | Baust .................... A61B 18/082 606/24 |
| 2013/0282038 A1 | 10/2013 | Dannaher et al. |
| 2014/0088577 A1* | 3/2014 | Anastassiou ......... A61B 18/201 606/17 |
| 2015/0141981 A1 | 5/2015 | Price et al. |
| 2015/0327930 A1* | 11/2015 | Bruno .................. A61B 5/0066 600/427 |
| 2016/0022305 A1 | 1/2016 | Lamping et al. |
| 2017/0000541 A1 | 1/2017 | Yates et al. |
| 2017/0202609 A1* | 7/2017 | Shelton, IV ....... A61B 18/1445 |
| 2018/0256129 A1* | 9/2018 | Govari ................... A61B 34/20 |

OTHER PUBLICATIONS

U.S. Appl. No. 62/509,351, entitled "Ultrasonic Instrument with Electrosurgical Features," filed May 22, 2017.

* cited by examiner

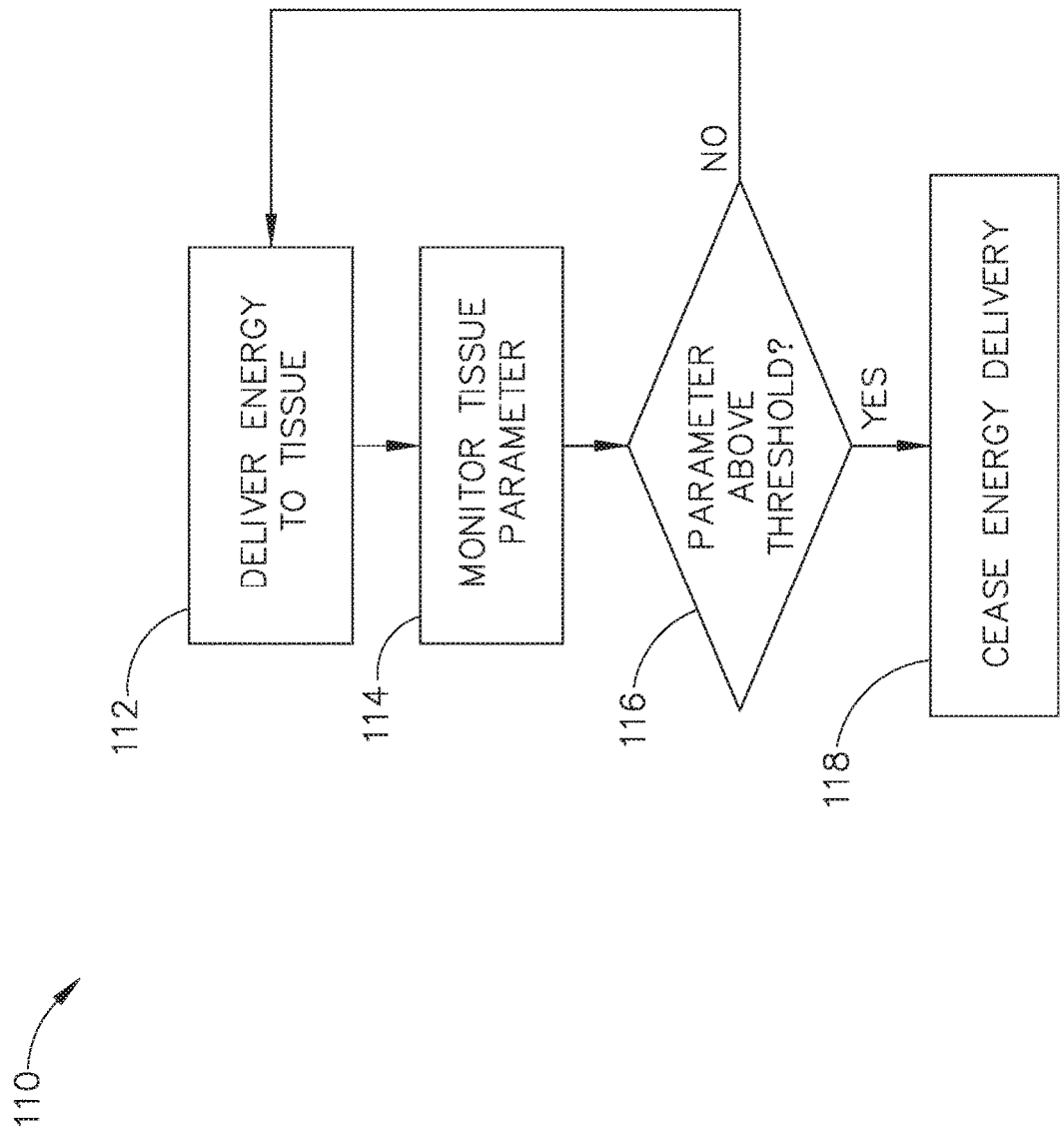

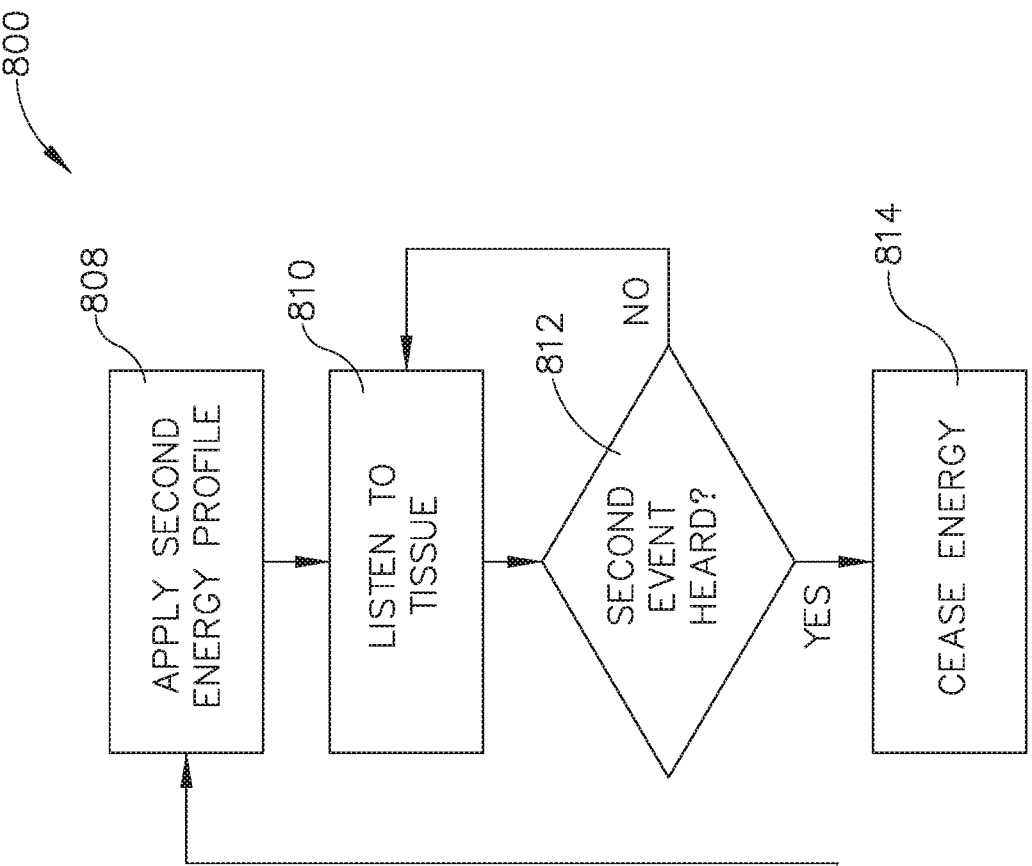
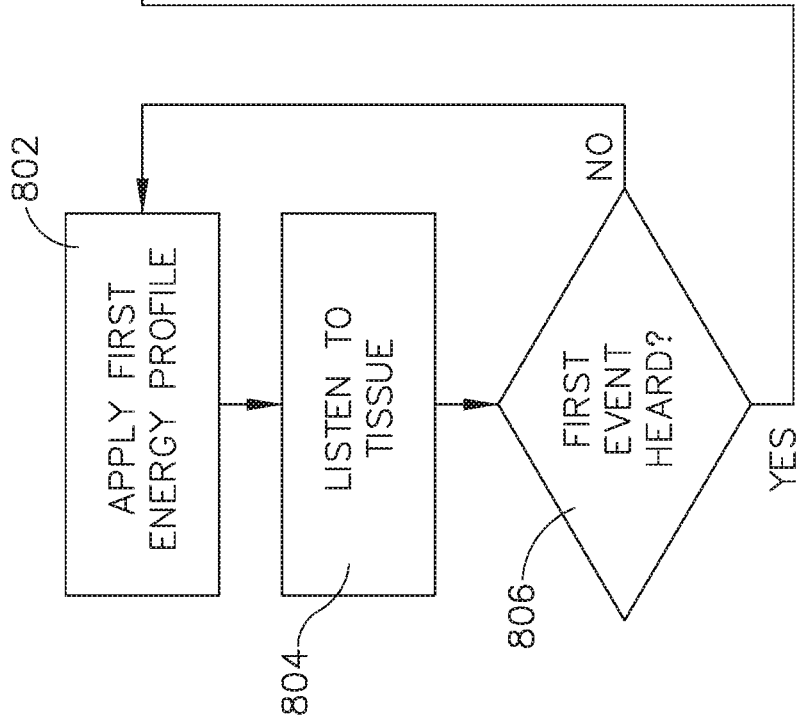
Fig. 11

APPARATUS AND METHOD TO CONTROL OPERATION OF SURGICAL INSTRUMENT BASED ON AUDIBLE FEEDBACK

BACKGROUND

Ultrasonic surgical instruments utilize ultrasonic energy for both precise cutting and controlled coagulation. Ultrasonic energy cuts and coagulates by vibrating a blade in contact with tissue. Vibrating at frequencies of approximately 55.5 kilohertz (kHz), for example, the ultrasonic blade denatures protein in the tissue to form a sticky coagulum. Pressure exerted on the tissue with the blade surface collapses blood vessels and allows the coagulum to form a hemostatic seal. The precision of cutting and coagulation may be controlled by the surgeon's technique and adjusting the power level, blade edge, tissue traction, and blade pressure, for example.

Examples of ultrasonic surgical devices include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pub. No. 2016/0022305, entitled "Ultrasonic Blade Overmold," published Jan. 28, 2016, now U.S. Pat. No. 9,750,521, issued Sep. 5, 2015, the disclosure of which is incorporated by reference herein.

Electrosurgical instruments utilize electrical energy for sealing tissue, and generally include a distally mounted end effector that can be configured for bipolar or monopolar operation. During bipolar operation, electrical current is provided through the tissue by active and return electrodes of the end effector. During monopolar operation, current is provided through the tissue by an active electrode of the end effector and a return electrode (e.g., a grounding pad) separately located on a patient's body. Heat generated by the current flowing through the tissue may form hemostatic seals within the tissue and/or between tissues, and thus may be particularly useful for sealing blood vessels, for example. The end effector of an electrosurgical device may also include a cutting member that is movable relative to the tissue and the electrodes to transect the tissue.

Electrical energy applied by an electrosurgical device can be transmitted to the instrument by a generator coupled with the instrument. The electrical energy may be in the form of radio frequency ("RF") energy, which is a form of electrical energy generally in the frequency range of approximately 300 kilohertz (kHz) to 1 megahertz (MHz). In use, an electrosurgical device can transmit such energy through tissue, which causes ionic agitation, or friction, in effect resistive heating, thereby increasing the temperature of the tissue. Because a sharp boundary is created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy works particularly well on connective tissue, which is primarily comprised of collagen and shrinks when contacted by heat.

An example of an RF electrosurgical device is the ENSEAL® Tissue Sealing Device by Ethicon Endo-Surgery, Inc., of Cincinnati, Ohio. Further examples of electrosurgical devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical devices and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; U.S. Pat. No. 9,545,253, entitled "Surgical Instrument with Contained Dual Helix Actuator Assembly," issued Jan. 17, 2017, the disclosure of which is incorporated by reference herein; and U.S. Pat. No. 9,572,622, entitled "Bipolar Electrosurgical Features for Targeted Hemostasis," issued Feb. 21, 2017, the disclosure of which is incorporated by reference herein.

Some instruments may provide ultrasonic and RF energy treatment capabilities through a single surgical device. Examples of such devices and related methods and concepts are disclosed in U.S. Pat. No. 8,663,220, entitled "Ultrasonic Surgical Instruments," issued Mar. 4, 2014, the disclosure of which is incorporated by reference herein; U.S. Pub. No. 2015/0141981, entitled "Ultrasonic Surgical Instrument with Electrosurgical Feature," published May 21, 2015, now U.S. Pat. No. 9,949,785, issued Apr. 24, 2018, the disclosure of which is incorporated by reference herein; and U.S. Pub. No. 2017/0000541, entitled "Surgical Instrument with User Adaptable Techniques," published Jan. 5, 2017, the disclosure of which is incorporated by reference herein.

Some surgical instruments include a microphone that is used to obtain audible feedback during operation of the instrument. An example of such an instrument is described in U.S. Pub. No. 2013/0282038, entitled "Surgical Instrument with Tissue Density Sensing," published Oct. 24, 2013, now U.S. Pat. No. 9,788,851, issued Oct. 17, 2017, the disclosure of which is incorporated by reference herein.

While various types of ultrasonic surgical instruments and electrosurgical instruments, including combination ultrasonic-electrosurgical devices, have been made and used, it is believed that no one prior to the inventor(s) has made or used the invention described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3 depicts a flowchart of an exemplary method of interrogating and sealing the tissue with the end effector of FIG. 2A;

FIG. 11 depicts a flowchart of another exemplary method of operating a surgical instrument based on audible feedback from tissue.

Figure 1:
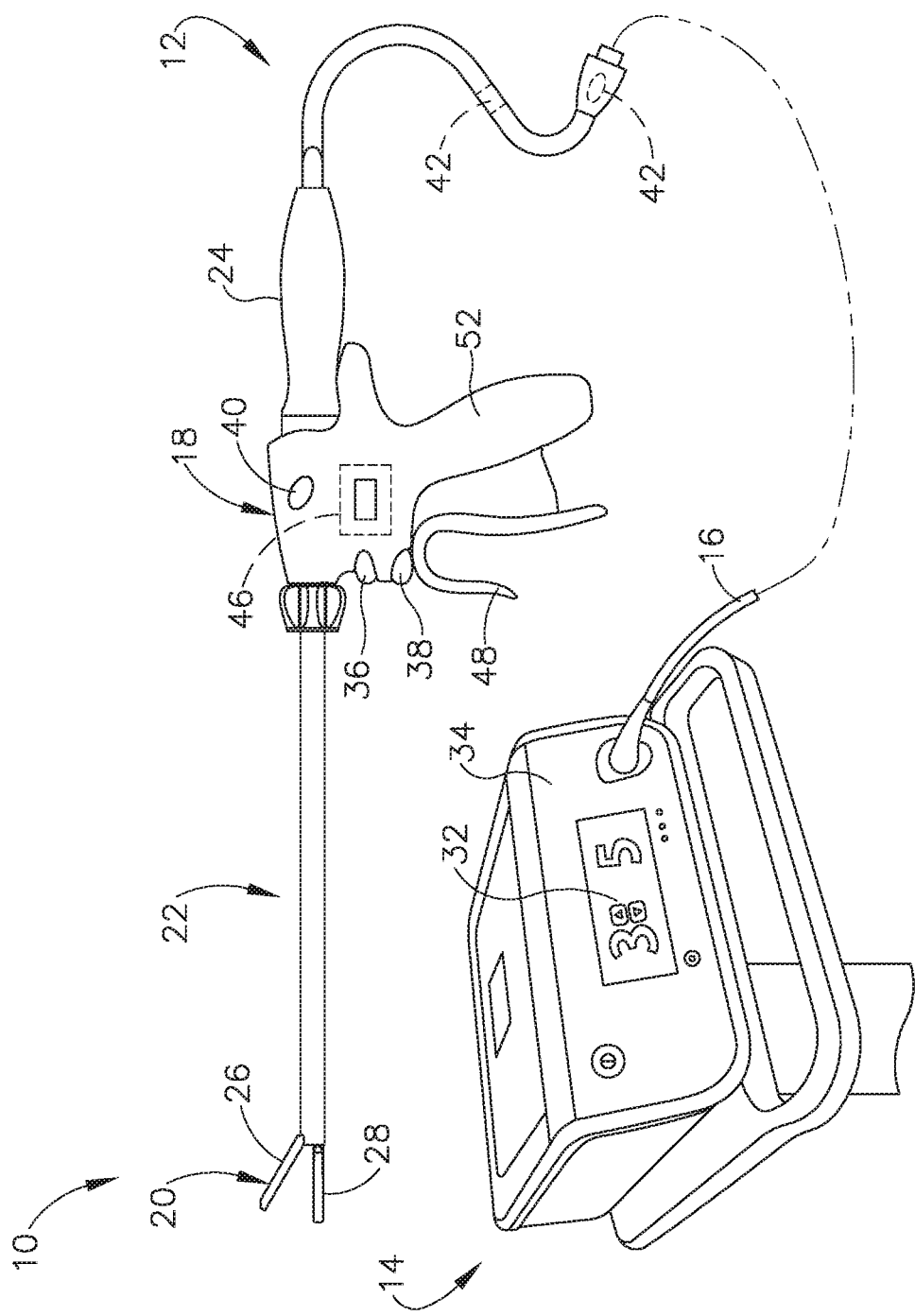
FIG. 1 depicts a schematic view of an exemplary ultrasonic surgical instrument including a shaft assembly and a handle assembly operatively connected to an ultrasonic generator.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical System

Figure 2A:
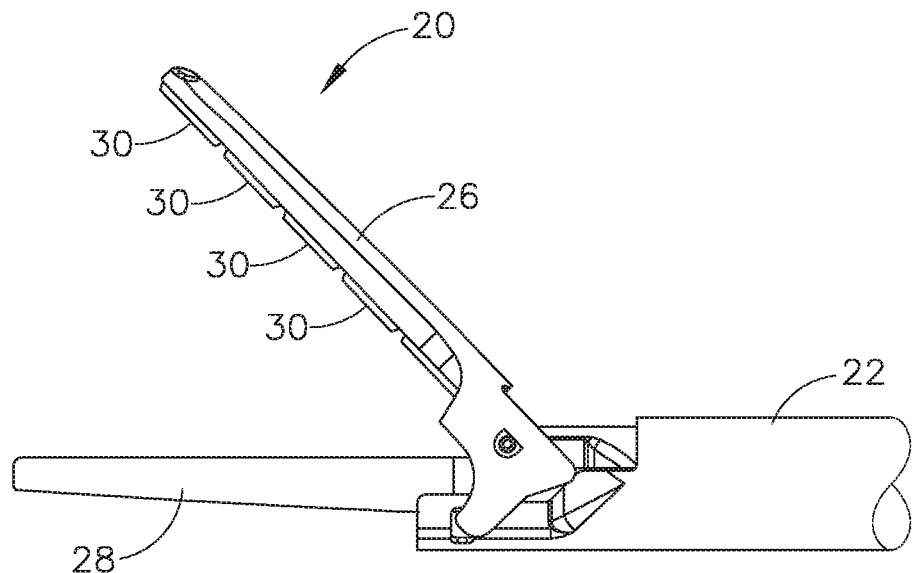
FIG. 2A depicts a side view of an end effector of the ultrasonic surgical instrument of FIG. 1 showing the end effector in an open configuration for receiving tissue of a patient.
Figure 2B:
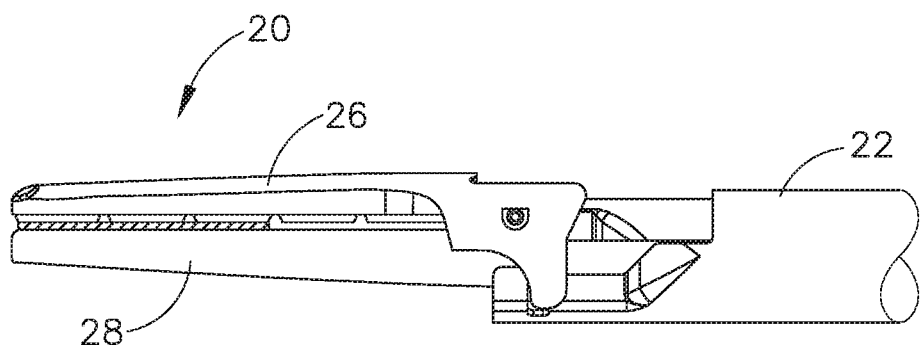
FIG. 2B depicts the side view of the end effector of FIG. 2A, but with the end effector in a closed configuration for clamping the tissue of the patient.

FIG. 1 illustrates one example of a surgical system (10) including a surgical instrument (12) and a generator (14) coupled via a cable (16). Surgical instrument (12) has a proximally positioned handle assembly (18), a distally positioned end effector (20), a shaft assembly (22) extending therebetween, and an ultrasonic transducer (24). End effector (20) generally includes a clamp arm (26) pivotally connected relative to an ultrasonic blade (28) and configured to pivot from an open position of an open configuration to a closed position of a closed configuration as discussed below in greater detail. Ultrasonic blade (28) is acoustically coupled with ultrasonic transducer (24) via an acoustic waveguide (not shown) for providing ultrasonic energy to ultrasonic blade (28). As shown in FIG. 2A, end effector (20) further includes a plurality of RF electrodes (30) positioned therealong for contacting the tissue in either the open or closed position as desired by a clinician. Generator (14) operatively connects to ultrasonic blade (28) and RF electrodes (30) to respectively provide ultrasonic energy and RF energy to ultrasonic blade (28) and RF electrodes (30) to thereby cut and/or seal the tissue is use.

In some versions, clamp arm (26) has two or more electrodes (30). In some such versions, electrodes (30) of clamp arm (26) are capable of applying bipolar RF energy to tissue. In some such versions, ultrasonic blade (28) remains electrically neutral, such that ultrasonic blade (28) is not part of the RF circuit. In some other versions, ultrasonic blade (28) forms part of the RF circuit, such that ultrasonic blade (28) cooperates with one or more electrodes (30) of clamp arm (26) to apply bipolar RF energy to tissue. By way of example only, some versions of clamp arm (26) may have just one electrode (30) that serves as an active pole for RF energy; while ultrasonic blade (28) provides a return pole for RF energy. Thus, the term "electrodes (30)" should be read to include versions where clamp arm (26) has only one single electrode.

It should be understood that terms such as "proximal" and "distal" are used herein with reference to surgical instrument (12). Thus, end effector (20) is distal with respect to the more proximal handle assembly (18). It will be further appreciated that for convenience and clarity, spatial terms such as "upper" and "lower" are used herein with respect to the drawings. However, surgical instruments are used in many orientations and positions, and these terms are not intended to be limiting and absolute. Likewise, terms such as "instrument" and "device" as well as "limit" and "cap" may be used interchangeably.

Generator (14) activates surgical instrument (12) to apply both ultrasonic and RF energies via end effector (20). Generator (14) is shown separate from surgical instrument (12) in the present example. In some other variations, generator (14) is integrated into handle assembly (18). In some such versions, handle assembly (18) also includes an integral power source (e.g., one or more batteries), such that handle assembly (18) is tetherless. In the present example, generator (14) generally includes an input device (32) located on a front panel (34) of generator (14). Input device (32) may have any suitable features that generate signals suitable for programming the operation of generator (14). For example, in operation, the clinician may program or otherwise control operation of generator (14) using input device (32) (e.g., by one or more processors contained in the generator) to control the operation of generator (14) (e.g., operation of the ultrasonic generator drive circuit (not shown) and/or the RF generator drive circuit (not shown)).

In various forms, input device (32) includes one or more buttons, switches, thumbwheels, keyboard, keypad, touch screen monitor, pointing device, remote connection to a general purpose or dedicated computer. In some versions, input device (32) has one or more user interface screens displayed on a touch screen monitor. Accordingly, the clinician may selectively set or program various operating parameters of generator (14), such as, current (I), voltage (V), frequency (f), and/or period (T) of a drive signal or signals generated by the ultrasonic and RF generator drive circuits (not shown). Specifically, in the present example, generator (14) is configured to deliver various power states to the surgical instrument (12) that include, but are not necessarily limited to, only ultrasonic energy, only RF energy, and a combination of ultrasonic and RF energies, which simultaneously powers ultrasonic blade (28) and RF electrodes (30). It will be appreciated that input device (32) may have any suitable features that generates signals suitable for programming the operation of generator (14) and is not unnecessarily limited to input device (32) shown and described herein.

By way of example only, generator (14) may comprise a GEN04 or GEN11 sold by Ethicon Endo-Surgery, Inc. of Cincinnati, Ohio. In addition, or in the alternative, generator (14) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein.

Surgical instrument (12) of the present example further includes a plurality of energy inputs, which are more particularly referred to herein as an upper button (36), lower button (38), and side button (40). By way of example, upper button (36) is configured to direct generator (14) to power ultrasonic transducer (24) with a maximum ultrasonic energy output, whereas lower button (38) is configured to direct generator (14) to power ultrasonic transducer (24) with a lower ultrasonic energy output. By way of further example, side button (40) is configured to direct generator (14) to power ultrasonic transducer (24) with a pulsed RF energy output, such as 5 continuous signals and 5 or 4 or 3 or 2 or 1 pulsed signals. In one or more examples, the specific drive signal configuration directed by energy inputs may be controlled and/or based upon EEPROM settings in generator (14) and/or user power level selection(s). By way of further example, surgical instrument (12) may include a two-button configuration for selectively directing ultrasonic and RF energies as described herein. Various examples of instruments having two-button input configurations are described in various patent references cited herein. In any case, it will be appreciated that the invention described herein is not intended to be unnecessarily limited to a particular configuration of input button(s), switch(es), etc. to the extent that any form of input may be so used.

Various processes and techniques described herein are performed by a controller (46), which includes internal logic, located in handle assembly (18). In some versions, controller (46) has at least one processor and/or other controller device in communication with generator (14), ultrasonic blade (28), RF electrodes (30), and other inputs and outputs described herein for monitoring and performing such processes and techniques. Also in some versions, controller (46) has a processor configured to monitor user input provided via one or more inputs and capacitive touch sensors. Controller (46) may also include a touch screen controller to control and manage the acquisition of touch data from a capacitive touch screen.

As shown in FIG. 1, handle assembly (18) further includes a trigger (48), which is operatively connected to clamp arm (26). Trigger (48) and clamp arm (26) are generally biased toward the unactuated, opened configuration. However, selectively manipulating trigger (48) proximally will pivot clamp arm (26) toward ultrasonic blade (28) from the open position to the closed position. As used in the present example, clamp arm (26) and ultrasonic blade (28) may also be generally referred to respectively as upper and lower jaws of surgical instrument (12). In the open position, clamp arm (26) and ultrasonic blade (28) are configured to receive the tissue, whereas clamp arm (26) is configured to clamp tissue against ultrasonic blade (28) for grasping, sealing, and/or cutting the tissue.

Ultrasonic blade (28) ultrasonically vibrates to seal and/or cut the tissue, whereas RF electrodes (30) provide electrical power to the tissue. RF electrodes (30) of the present example are all electrically similar electrodes, with ultrasonic blade (28) also electrically connected as a return electrode. As used therein, the term "electrode" may thus apply to both RF electrodes (30) and ultrasonic blade (28) with respect to the RF electrical circuit. Without contacting tissue, the electrical circuit from RF electrodes (30) to ultrasonic blade (28) is open; whereas the electrical circuit is closed by the tissue between RF electrode (30) and ultrasonic blade (28) in use. RF electrodes (30) may be activated to apply RF energy alone or in combination with ultrasonic activation of ultrasonic blade (28). For example, activating only RF electrodes (30) to apply RF energy alone may be used for spot coagulating without concern for inadvertently cutting tissue with ultrasonically activated ultrasonic blade (28). However, the combination of ultrasonic energy and RF energy may be used for sealing and/or cutting tissue to achieve any combination of diagnostic or therapeutic effects, various examples of which will be described below in greater detail.

In addition to applying RF electrosurgical energy to tissue, electrodes (30), alone or in combination with ultrasonic blade (28), may be used to measure the electrical impedance of tissue. Such tissue impedance may be measured before, during, and/or after delivery of ultrasonic energy to the tissue by ultrasonic blade (28). In addition, or in the alternative, such tissue impedance may be measured before, during, and/or after delivery of RF energy to the tissue by electrodes (30), alone or in combination with ultrasonic blade (28). The data from the measured tissue impedance may be used in various ways as will be apparent to those of ordinary skill in the art, including the exemplary ways described in greater detail below.

As noted above, generator (14) is a single output generator that can deliver power through a single port to provide both RF and ultrasonic energy such that these signals can be delivered separately or simultaneously to end effector (20) for cutting and/or sealing tissue. Such a single output port generator (14) has a single output transformer with multiple taps to provide power, either for RF or for ultrasonic energy, to end effector (20) depending on the particular treatment being performed on the tissue. For example, generator (14) may deliver energy with higher voltage and lower current to drive ultrasonic transducer (24), with lower voltage and higher current as required to drive RF electrodes (30) for sealing tissue, or with a coagulation waveform for spot coagulation using either monopolar or bipolar electrosurgical electrodes. The output waveform from generator (14) can be steered, switched, or filtered to provide the desired frequency to end effector (20) of surgical instrument (12).

The particular diagnostic and/or therapeutic effects associated with various treatments may be adjusted in use with controller (46) monitoring, directing, and adjusting aspects of the ultrasonic and RF energies in conjunction with one or more tissue properties, which may even change for adjustment in real-time. Such tissue properties may include, but need not be limited to, tissue type, tissue thickness, tissue density, and/or the electrical impedance of the tissue. As described in further detail below, such tissue properties may further include sounds emitted by the tissue as end effector (20) applies ultrasonic and/or RF energy to the tissue.

FIG. 3 shows an exemplary method (110) of sealing tissue with surgical system (10). In this method (110), controller (46) executes an algorithm to ensure that end effector (20) applies enough energy to seal tissue without cutting the tissue. In a first step (block 112), the clinician activates end effector (20) to deliver ultrasonic energy and/or RF energy to tissue that is engaged by end effector (20). While end effector (20) engages the tissue and applies energy to the tissue, controller (46) monitors one or more parameters of the tissue (block 114), such as by sensing electrical impedance of the tissue and/or other properties of the tissue. Based on the feedback from the tissue in response to the monitoring (block 114), controller (46) determines (block 116) whether one or more parameters are above a threshold value. If the determination (block 116) reveals that the value is below the threshold, controller (46) continues to direct end effector (20) to deliver energy to the tissue (block 112); and continues the monitoring (block 114) of one or more tissue parameters. Once the value exceeds the threshold (e.g., a value associated with the tissue reaching a sealed state), controller (46) ceases the delivery of energy (block 118) via end effector (20). In some variations, before the value exceeds the threshold, controller (46) adjusts the power profile of the energy delivered via end effector (20), based on the data received through monitoring (block 114). Such adjustments may be made to avoid severing the tissue and/or to avoid other results that might be undesirable for the particular operation at hand.

While method (110) of the foregoing example seeks to seal tissue without cutting the tissue, method (110) may be readily modified to achieve various other effects on tissue. For instance, as will be described in greater detail below, method (110) may be modified to provide a first energy delivery profile until the tissue is cut; then automatically transition to a second energy delivery profile after tissue monitoring (block 114) reveals that the tissue has been cut; then automatically cease delivery of energy after tissue monitoring (block 114) reveals that the tissue has been sealed.

Figure 4:
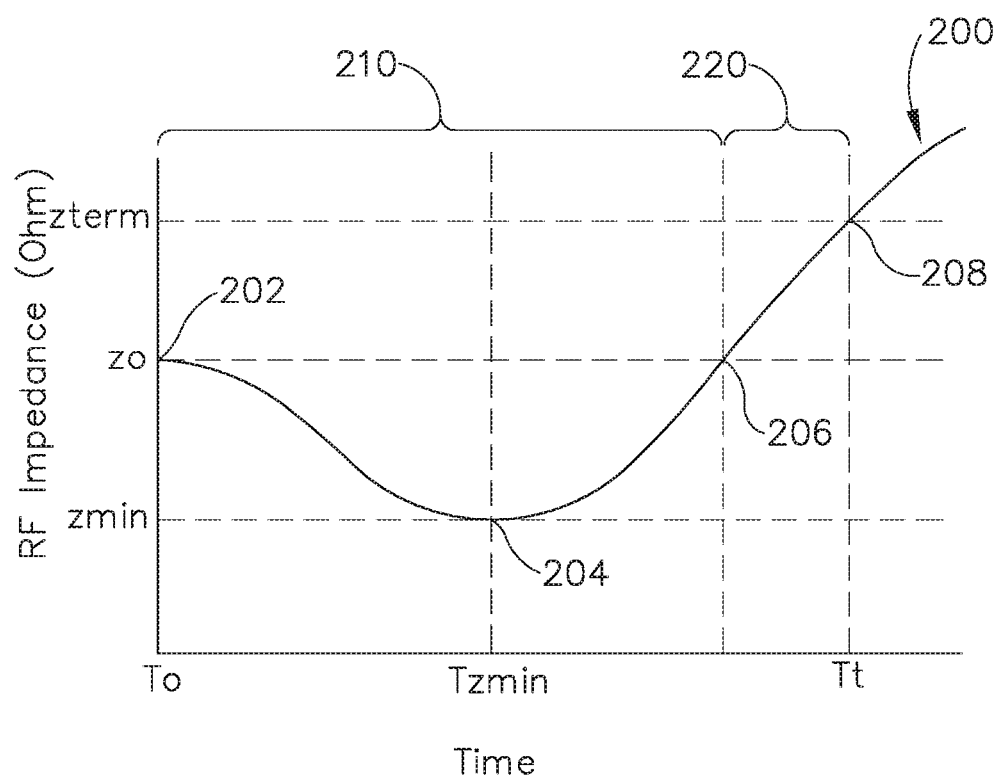
FIG. 4 depicts a graph plotting tissue impedance over time as the end effector of FIG. 2A applies ultrasonic energy to the tissue.

FIG. 4 shows an exemplary curve (200) representing tissue impedance that may be sensed during monitoring (block 114) as ultrasonic energy is delivered to the tissue (block 112) over a course of time. As shown, the tissue impedance value starts at an initial value (202) and begins to fall. The tissue impedance value eventually reaches a minimum value (204) before rising again. After a first duration (210), the tissue impedance value reaches a value (206) that is the same as the initial value (202). Controller (46) allows the energy delivery (block 112) to continue until the tissue impedance reaches a terminal level (208), which occurs after a second duration (220). Once the tissue impedance reaches terminal level (208), the tissue is assumed to have reached an appropriately sealed state, and controller (46) terminates the delivery of energy to the tissue (block 118). In other words, this terminal impedance level (208) may serve as the threshold value for query (block (116) of method (110).

In addition to the foregoing, surgical system (10) may be configured and/or operable in accordance with at least some of the teachings of U.S. Pat. App. No. 62/509,336, entitled "Control Algorithm for Surgical Instrument with Ultrasonic and Electrosurgical Modalities," filed May 22, 2017, the disclosure of which is incorporated by reference herein; U.S. Pat. App. No. 62/509,351, entitled "Ultrasonic Instrument with Electrosurgical Features,' filed May 22, 2017, the disclosure of which is incorporated by reference herein; and/or any other references cited herein. Further exemplary modifications will be described in greater detail below.

II. Exemplary Surgical System with Acoustic Monitoring of Tissue

As noted above, it may be desirable to monitor the electrical impedance of tissue and/or other parameters of tissue as energy is being delivered to tissue, to identify the state of the tissue, and to adjust the delivery of energy to the tissue accordingly. In some instances, the sounds emitted by the tissue may serve as a meaningful indicator of tissue state, such that the sounds emitted by the tissue may be used to modify the delivery of energy to the tissue. For instance, when tissue is being sealed by applying ultrasonic and/or RF electrosurgical energy to the tissue, the tissue may initially be relatively silent. Once the tissue has reached a certain temperature associated with the tissue achieving a sealed state, the tissue may start to hiss or sizzle, thereby emitting an audible sound indicating that the tissue is reaching or has reached a sealed state. For instance, when the tissue reaches a certain temperature, fluid it the tissue may begin to boil or otherwise bubble, and the emission/bursting of these bubbles may cause the hissing or sizzling sound. If the energy delivery continues, the hissing or sizzling sound may eventually cease, indicating that that the seal is complete. It may therefore be desirable to provide a modified version of surgical instrument (12) that is capable of monitoring and reacting to sounds emitted by tissue as the modified surgical instrument (12) delivers energy to the tissue.

Figure 5:
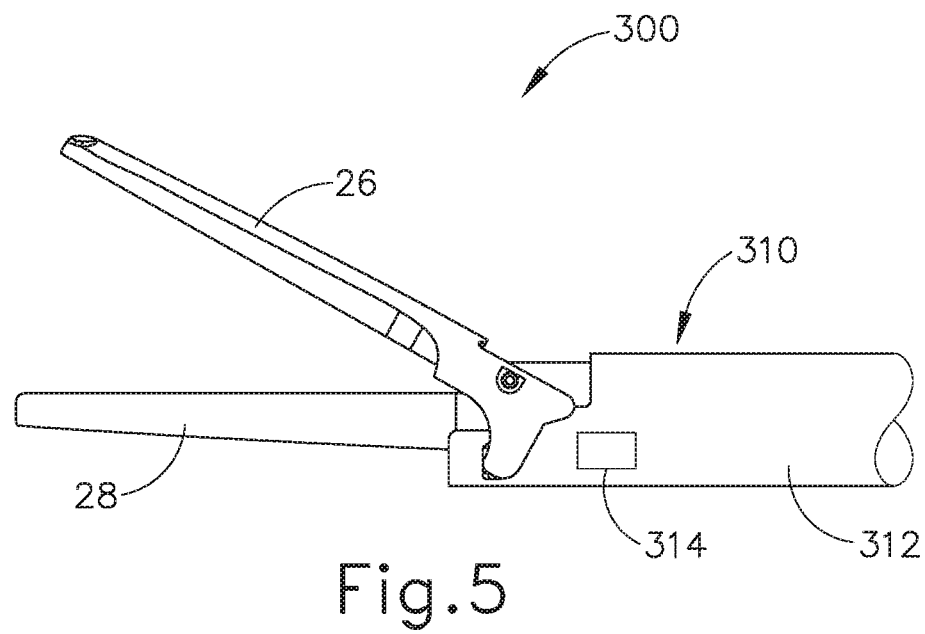
FIG. 5 depicts a side view of an exemplary variation of the end effector of FIG. 2A, including a microphone.

FIG. 5 shows an exemplary modified end effector (300) and shaft assembly (310) that may be readily incorporated into surgical instrument (12). Like end effector (20), end effector (300) of this example has pivoting clamp arm (26) and an ultrasonic blade (28). Shaft assembly (310) includes an outer sheath (312) and a microphone (314) at the distal end of outer sheath (312). In some versions, microphone (314) is located on the exterior of outer sheath (312). In some other versions, microphone (314) is located in the interior of outer sheath (312). In still other versions, one or more microphones (314) are located on the exterior of outer sheath (312) and/or one or more microphones (314) are located in the interior of outer sheath (312). As yet another merely illustrative example, one or more microphones (314) may be secured on and/or in clamp arm (26); and/or on and/or in ultrasonic blade (28). Various suitable locations for one or more microphones (314) will be apparent to those of ordinary skill in the art in view of the teachings herein. In the present example, microphone (314) is positioned and operable to capture sound emitted by tissue as end effector (20) delivers ultrasonic and/or RF energy to the tissue.

Figure 6:
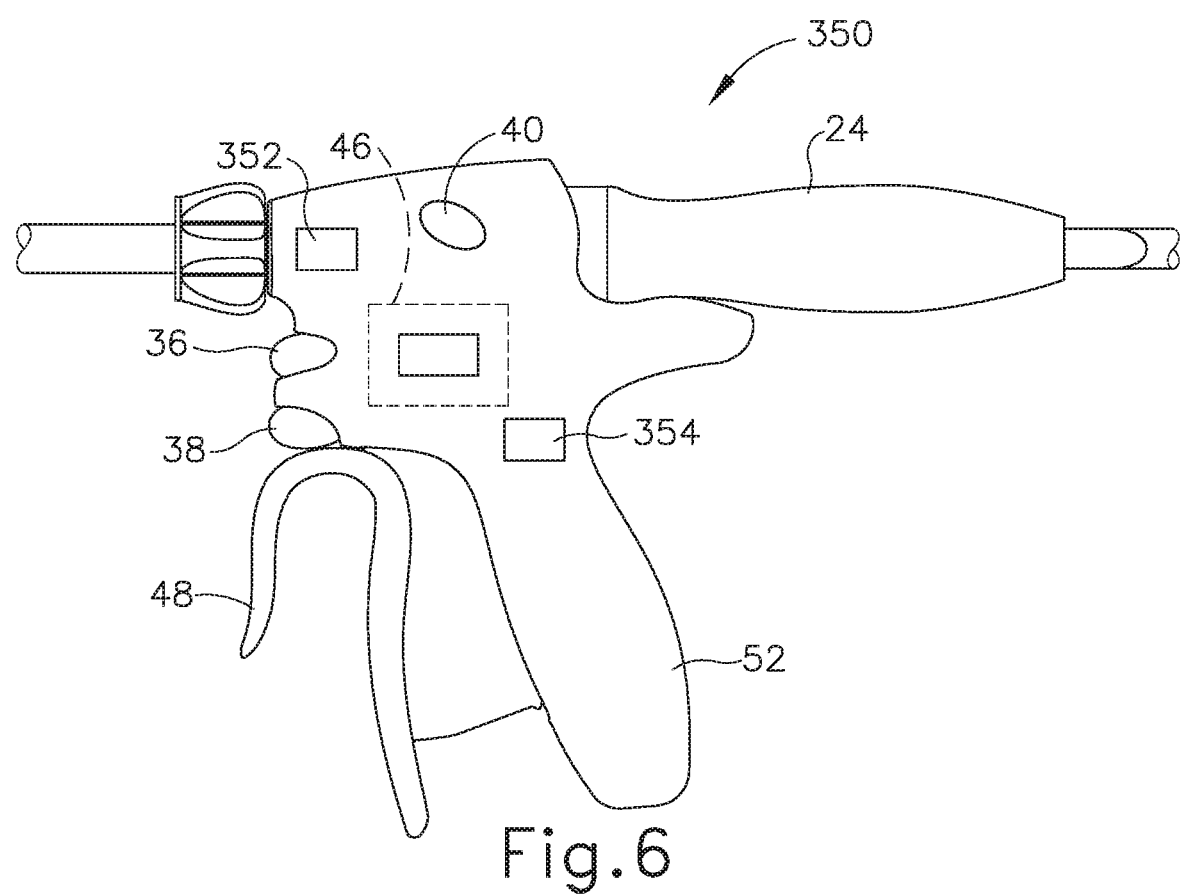
FIG. 6 depicts a side view of an exemplary variation of the handle assembly of FIG. 1, including a microphone and a user feedback feature.

FIG. 6 shows an exemplary modified handle assembly (350) that may be readily incorporated into surgical instrument (12). Except as otherwise described below, handle assembly (350) may be configured and operable just like handle assembly (18), such that like reference numerals will be used to indicate like elements. Unlike handle assembly (18), handle assembly (350) of this example includes a microphone (352) and a user feedback feature (354). Microphone (352) is configured to detect sounds within the operating room (e.g., ambient noise). In some instances, the sound data from microphone (352) is used to provide noise cancelling with respect to sound captured by microphone (314), such that controller (46) is thereby able to process sound captured by microphone (314) with ambient noise from the operating room being cancelled out. Other suitable uses for microphone (352) will be apparent to those of ordinary skill in the art in view of the teachings herein. In some other versions, microphone (352) is omitted.

User feedback feature (354) is configured to provide the operator with one or more forms of feedback relating to the state of the tissue engaged by end effector (300). In some versions, user feedback feature (354) is configured to provide visual feedback via a display screen, one or more LEDs and/or any other suitable kind(s) of features that are operable to provide visual feedback to a user. In addition, or in the alternative, user feedback feature (354) may be configured to provide audible feedback via a speaker or some other sound-emitting feature. Such audible feedback may come in the form of one or more tones, vocal statements, and/or other forms of audible feedback. In addition, or in the alternative, user feedback feature (354) may be configured to provide haptic feedback. For instance, user feedback feature (354) may cause pistol grip (52) to vibrate in one or more patterns. Other suitable forms that user feedback feature (354) may take, and different kinds of user feedback that may be provided via user feedback feature (354), will be apparent to those of ordinary skill in the art in view of the teachings herein. In some other versions, user feedback feature (354) is omitted.

Figure 7:
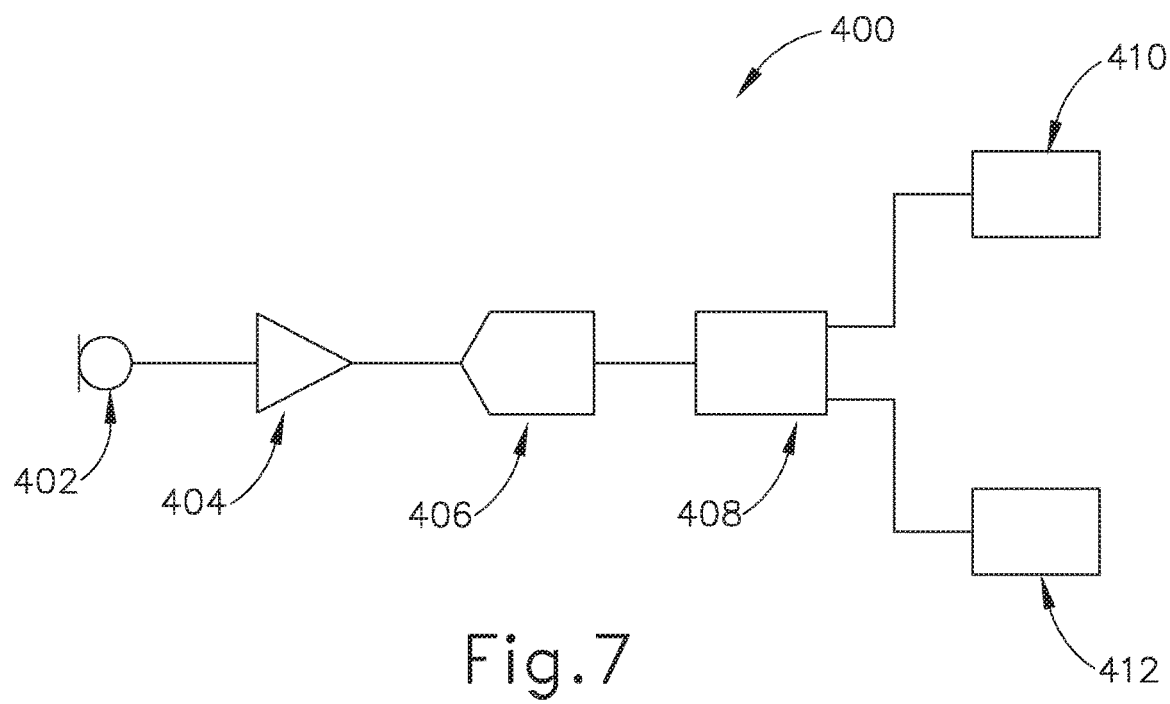
FIG. 7 depicts a schematic diagram of an exemplary circuit for processing audible feedback from tissue.

FIG. 7 shows an exemplary circuit (400) that may be incorporated into a version of surgical system (10) that includes end effector (300) and handle assembly (350). Circuit (400) of this example includes a microphone (402), an amplifier (404), an analog-digital converter (406), a microprocessor (408), a user feedback feature (410), and an energy control module (412). Microphone (402) may comprise microphone (314), microphone (352), and/or any other microphone(s). Amplifier (404) comprises a conventional amplifier that is configured to amplify the signal from microphone (402). In the event that more than one microphone (402) is used, each microphone (402) may have its own dedicated amplifier (404). Analog-digital converter (406) comprises a conventional converter that is operable to convert an analog signal from microphone (402), as amplified by amplifier (404) into a digital signal. Microprocessor (408) is configured to execute an algorithm to process the digital signal and drive user feedback feature (410) and/or energy control module (412) accordingly.

User feedback feature (410) may comprise user feedback feature (354) of handle assembly (350). In addition, or in the alternative, user feedback feature (410) may be incorporated into a variation of generator (14). An example of how microprocessor (408) may drive user feedback feature (410) based on data from microphone (402) will be described below with reference to FIG. 10. Energy control module (412) is operable to vary the delivery of energy via end effector (300), such as by ceasing delivery of ultrasonic energy, transitioning to delivery of RF energy, ceasing delivery of RF energy, etc. Examples of how microprocessor (408) may drive energy control module (412) based on data from microphone (402) will be described below with reference to FIG. 11.

Figure 8:
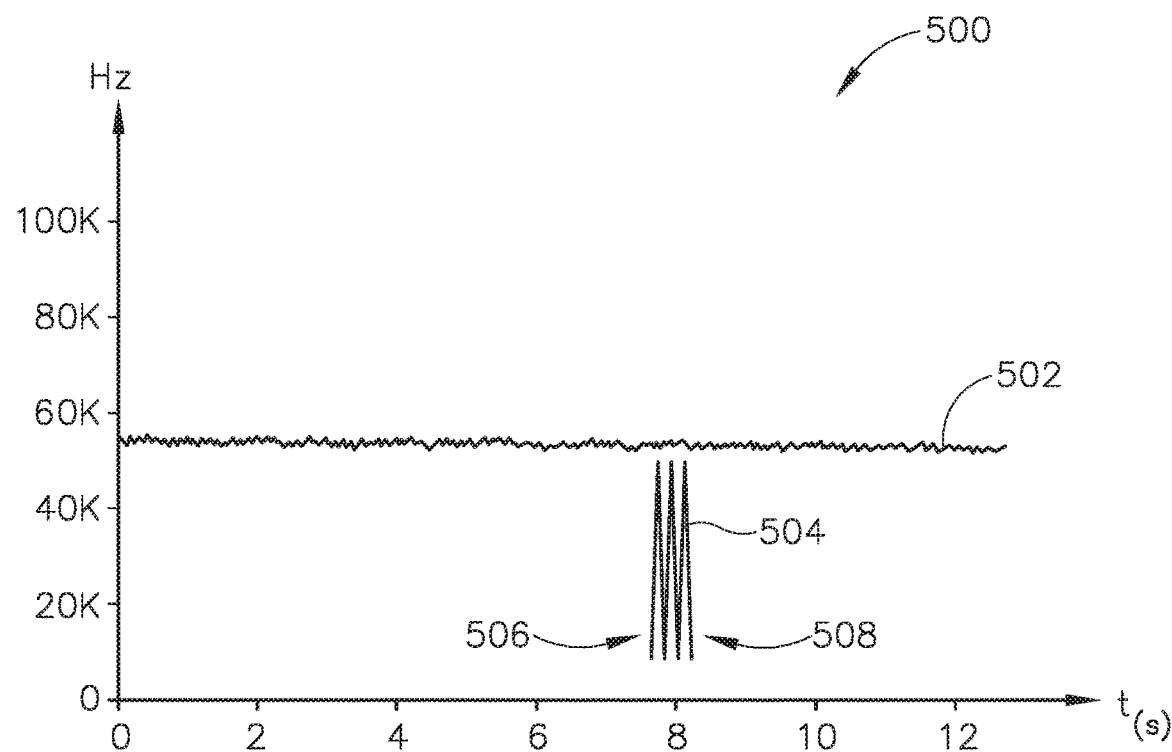
FIG. 8 depicts a graph plotting audible feedback from tissue over time.

FIG. 8 shows a graph (500) with a first plot (502) and a second plot (504). Graph (500) includes a time axis that begins when ultrasonic blade (28) is activated while tissue is clamped between clamp arm (26) and ultrasonic blade (28). First plot (502) represents the sound of active ultrasonic blade (28), as captured by microphone (314). In the present example, ultrasonic blade (28) resonates at an ultrasonic frequency of approximately 55 kHz, so this resonant vibration is picked up by microphone (314) as a persistent audible "ringing" sound at approximately 55 kHz. Second plot (504) represents the sound of the clamped tissue. As shown, the tissue is silent for over 7 seconds. Just before the 8-second mark, the tissue begins to hiss or sizzle, such that microphone (314) picks up this sound at a starting point (506). This hissing or sizzling continues until just after the 8-second mark, where the sound ceases at an ending point (508). The tissue begins sealing in response to the activated ultrasonic blade (28) at starting point (506). At ending point (508) the tissue sealing is complete. As shown, the hissing or sizzling sound of the tissue spans across a relatively wide frequency spectrum, such that it is easily distinguishable from the persistent ringing of ultrasonic blade (28). Of course, the frequency spectrum shown in FIG. 8, and the approximately 8-second time frame shown in FIG. 8, are merely illustrative examples. Different frequency and timing parameters may be observed in different contexts.

III. Exemplary Method of Processing Acoustic Feedback from Tissue

Figure 9:
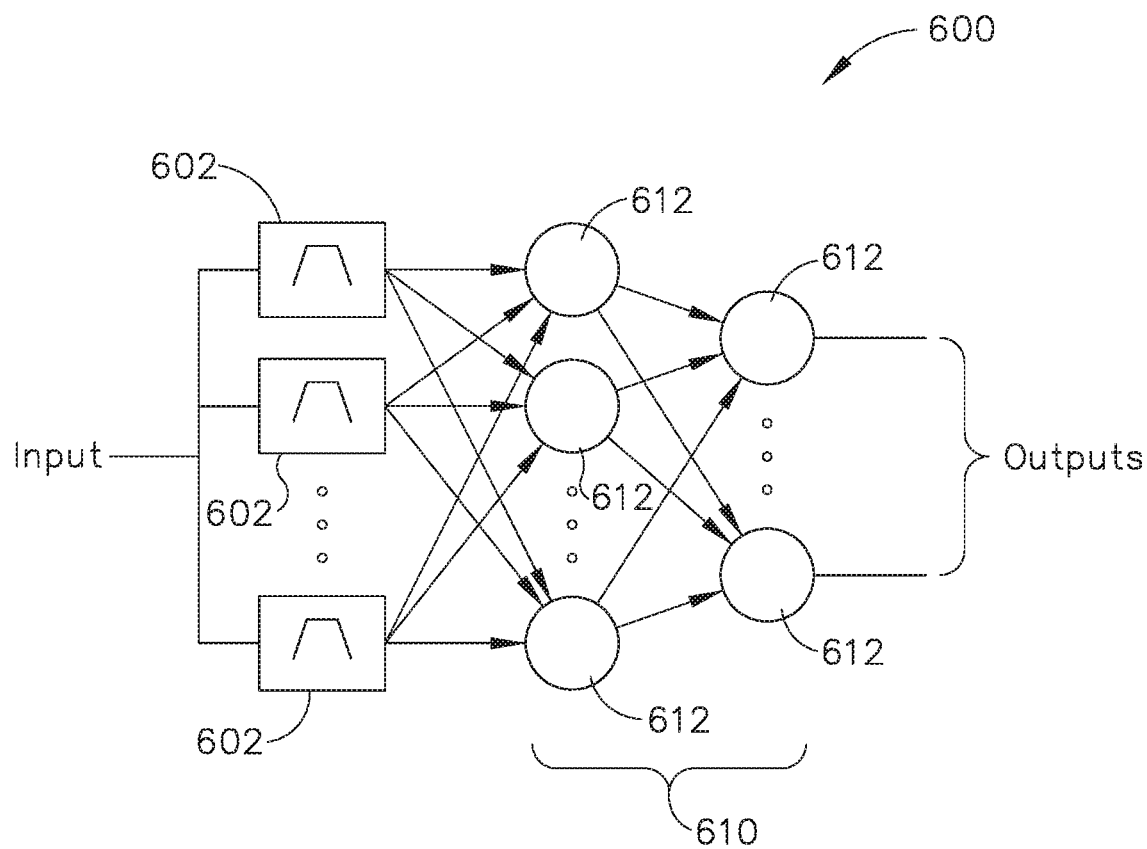
FIG. 9 depicts a schematic diagram of another exemplary circuit for processing audible feedback from tissue.

As noted above, acoustic feedback from tissue, as captured by one or more microphones (314, 402), may be processed in numerous different ways. FIG. 9 shows an exemplary processing system (600) where the input signal from microphone (314, 402) is passed through several band-pass filters (602), which are operable to isolate several frequency windows of the spectrum found in the input signal from microphone (314, 402). In a second stage of processing system (600), the outputs of band-pass filters (602) are communicated through a neural network (610) having several nodes (612). Neural network (610) processes the signal to recognize the onset (506) and cessation (508) of the hissing or sizzling sound (504). In some variations, the second stage provides fuzzy logic to process the signal. It should also be understood that at least some of processing system (600) may be embodied in microprocessor (408) and/or otherwise within circuit (400). Other suitable forms that processing system (600) may take will be apparent to those of ordinary skill in the art in view of the teachings herein.

Figure 10:
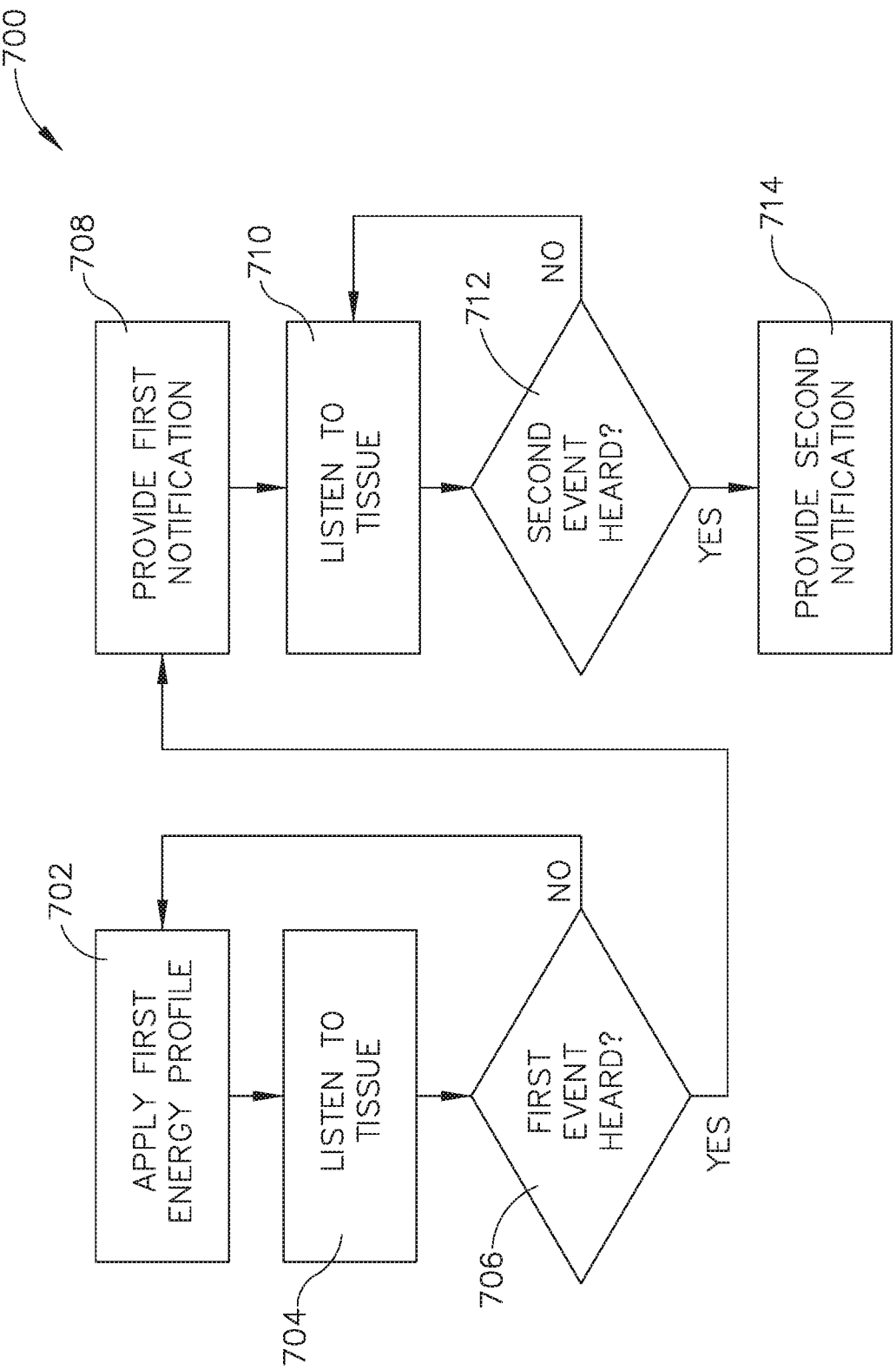
FIG. 10 depicts a flowchart of an exemplary method of operating a surgical instrument based on audible feedback from tissue.

FIG. 10 shows an exemplary method (700) where a modified version of surgical system (10) provides user feedback based on acoustic feedback from tissue. In this example, method (700) begins with the application of energy to tissue via end effector (300) (block 702). Such energy may include ultrasonic energy, RF energy, a combination of ultrasonic and RF energy, or some other form of energy. Microphone (314, 402) listens to the tissue (block 704) while the energy is being applied to the tissue. The acoustic feedback from the tissue is processed to "listen" for a first event (block 706). For instance, this first event may be the starting point (506) of a hissing or sizzling sound (504). Other meaningful sounds that may be emitted from tissue will be apparent to those of ordinary skill in the art in view of the teachings herein. The listening query (block 706) may be carried out by processing system (600), some other variation of microprocessor (408), or otherwise. If the starting point (506) of a hissing or sizzling sound (504) is not detected, energy continues to be applied (block 702) and the listening (block 704) continues.

Once the starting point (506) of a hissing or sizzling sound (504) is detected, a first notification is provided to the user (block 708). This first notification may be provided via user feedback feature (410). As noted above, user feedback feature (410) may be embodied in user feedback feature (354) of handle assembly (350); and/or in some feature of generator (14). The first notification may be audible, visual, and/or haptic. After receiving the first notification (block 708), the operator may manually change their operation of surgical instrument (12). For instance, the operator may actuate a different button (36, 38, 40) or provide some other response. Alternatively, the operator may simply observe the first notification (block 708) without changing their operation of surgical instrument (12).

After providing the first notification (block 708), microphone (314, 402) listens again to the tissue (block 710) while the energy is applied to the tissue. This energy may be the same as the energy applied (block 702) of the method (700); or it may have been changed based on manual user input from the operator. The acoustic feedback from the tissue is processed to "listen" for a second event (block 712). For instance, this first event may be the ending point (508) of a hissing or sizzling sound (504). Other meaningful second acoustic events may occur with respect to tissue will be apparent to those of ordinary skill in the art in view of the teachings herein. The listening query (block 712) may be carried out by processing system (600), some other variation of microprocessor (408), or otherwise. If the ending point (508) of a hissing or sizzling sound (504) is not detected, energy continues to be applied and the listening (block 710) continues.

Once the ending point (508) of a hissing or sizzling sound (504) is detected, a second notification is provided to the user (block 714). This first notification may be provided via user feedback feature (410). As noted above, user feedback feature (410) may be embodied in user feedback feature (354) of handle assembly (350); and/or in some feature of generator (14). The second notification may be audible, visual, and/or haptic. After receiving the second notification (block 714), the operator may manually change their operation of surgical instrument (12). For instance, the operator may actuate a different button (36, 38, 40) or provide some other response. Alternatively, the operator may deactivate end effector (300) (e.g., by releasing button (36, 38, 40)) and thereby cease application of energy to tissue via end effector (300).

FIG. 11 shows an exemplary method (800) where a modified version of surgical system (10) varies the power profile of energy delivered via end effector (300) based on acoustic feedback from tissue. In this example, method (800) begins with the application of energy to tissue via end effector (300) (block 802). Such energy may include ultrasonic energy, RF energy, a combination of ultrasonic and RF energy, or some other form of energy. Microphone (314, 402) listens to the tissue (block 804) while the energy is being applied to the tissue. The acoustic feedback from the tissue is processed to "listen" for a first event (block 806). For instance, this first event may be the starting point (506) of a hissing or sizzling sound (504). Other meaningful sounds that may be emitted from tissue will be apparent to those of ordinary skill in the art in view of the teachings herein. The listening query (block 806) may be carried out by processing system (600), some other variation of microprocessor (408), or otherwise. If the starting point (506) of a hissing or sizzling sound (504) is not detected, energy continues to be applied (block 802) and the listening (block 804) continues.

Once the starting point (506) of a hissing or sizzling sound (504) is detected, a second energy profile is applied to the tissue (block 808) via end effector (300). The following table lists several merely illustrative kinds of energy profiles that may be applied (block 802, block 808).

TABLE 1

| Example | First Energy Profile | Second Energy Profile |
| --- | --- | --- |
| 1 | Ultrasonic energy only, at first set of parameters | Ultrasonic energy only, at second set of parameters |
| 2 | RF energy only, at first set of parameters | RF energy only, at second set of parameters |

TABLE 1-continued

| Example | First Energy Profile | Second Energy Profile |
|---|---|---|
| 3 | Ultrasonic and RF energy at first set of parameters | Ultrasonic and RF energy at second set of parameters |
| 4 | Ultrasonic energy only | RF energy only |
| 5 | RF energy only | Ultrasonic energy only |

Other suitable variations of first and second energy profiles will be apparent to those of ordinary skill in the art in view of the teachings herein.

After applying the second energy profile (block 808), microphone (314, 402) listens again to the tissue (block 810) while the second energy profile is applied to the tissue. The acoustic feedback from the tissue is processed to "listen" for a second event (block 812). For instance, this first event may be the ending point (508) of a hissing or sizzling sound (504). Other meaningful second acoustic events may occur with respect to tissue will be apparent to those of ordinary skill in the art in view of the teachings herein. The listening query (block 812) may be carried out by processing system (600), some other variation of microprocessor (408), or otherwise. If the ending point (508) of a hissing or sizzling sound (504) is not detected, the second energy profile continues to be applied and the listening (block 810) continues.

Once the ending point (508) of a hissing or sizzling sound (504) is detected, the energy to tissue is ceased (block 814). Alternatively, a third energy profile may be applied. Other suitable variations of method (800) will be apparent to those of ordinary skill in the art in view of the teachings herein.

While methods (700, 800) are shown separately in different drawings, methods (700, 800) may in fact be performed simultaneously by the same modified version of surgical system (10). For instance, the first notification can be provided (block 708) at the same time the second energy profile is provided (block 808). Similarly, the second notification can be provided (block 714) at the same time the delivery of energy is ceased (block 814). Other suitable ways in which user feedback may be provided in combination with automated variation of power profiles, based at least in part on acoustic feedback from tissue, will be apparent to those of ordinary skill in the art in view of the teachings herein.

While the foregoing examples are provided in the context of user feedback and/or automated variation of power profiles being provided in response to acoustic feedback from tissue, some other variations may factor in other sensed tissue parameters. For instance, some control algorithms may factor in both acoustic feedback from tissue and sensed electrical impedance of tissue to influence how the control algorithm is executed. Other suitable kinds of tissue parameters that may be combined with acoustic feedback from tissue, in order to execute a control algorithm, will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a shaft assembly extending distally from the body, wherein the shaft assembly has a distal end; (c) an end effector located at the distal end of the shaft assembly, wherein the end effector is operable to apply energy to tissue and thereby change a state of the tissue; (d) a first acoustic sensor configured to pick up sound emitted by tissue; and (e) a processor in communication with the first acoustic sensor, wherein the processor is configured to provide an automated response in response to a signal from the first acoustic sensor indicating a change in the state of the tissue.

Example 2

The apparatus of Example 1, wherein the first acoustic sensor is secured to the distal end of the shaft assembly.

Example 3

The apparatus of any one or more of Examples 1 through 2, wherein the first acoustic sensor is secured to the end effector.

Example 4

The apparatus of any one or more of Examples 1 through 3, wherein the first acoustic sensor comprises a microphone.

Example 5

The apparatus of any one or more of Examples 1 through 4, further comprising a second acoustic sensor.

Example 6

The apparatus of Example 5, wherein the second acoustic sensor is located in the body.

Example 7

The apparatus of any one or more of Examples 5 through 6, wherein the processor is further configured to cancel out ambient noise picked up by the second acoustic sensor and thereby filter the signal from the first acoustic sensor.

Example 8

The apparatus of any one or more of Examples 1 through 7, further comprising a user feedback feature, wherein the processor is configured to provide an automated notification to an operator via the user feedback feature.

Example 9

The apparatus of Example 8, wherein the user feedback feature is located in or on the body.

Example 10

The apparatus of any one or more of Examples 8 through 9, further comprising a generator, wherein the generator is configured to provide power to drive the end effector, wherein the generator is remotely located relative to the body, wherein the user feedback feature is located in or on the generator.

Example 11

The apparatus of any one or more of Examples 8 through 10, wherein the processor is configured to provide a first automated notification to an operator via the user feedback feature in response to a signal from the first acoustic sensor indicating a first change in the state of the tissue, wherein the processor is further configured to provide a second automated notification to an operator via the user feedback feature in response to a signal from the first acoustic sensor indicating a second change in the state of the tissue.

Example 12

The apparatus of any one or more of Examples 1 through 11, wherein the processor is configured to provide an automated response in response to a signal from the first acoustic sensor indicating a change in the state of the tissue by changing an energy profile associated with the energy applied to the tissue.

Example 13

The apparatus of Example 12, wherein the processor is configured to change an energy profile via the end effector in response to a signal from the first acoustic sensor indicating a first change in the state of the tissue, wherein the processor is further configured to cease delivery of energy to the tissue via the end effector in response to a signal from the first acoustic sensor indicating a second change in the state of the tissue.

Example 14

The apparatus of any one or more of Examples 1 through 13, wherein the end effector is operable to apply ultrasonic energy to tissue.

Example 15

The apparatus of any one or more of Examples 1 through 14, wherein the end effector is operable to apply RF energy to tissue.

Example 16

A method of operating on tissue, the method comprising: (a) applying energy to the tissue via an end effector of a surgical instrument; (b) listening to the tissue with an acoustic sensor; (c) processing a signal from the acoustic sensor to detect a first change in state of the tissue, wherein the state of the tissue changes in response to the energy applied via the end effector; and (d) automatically providing a first notification to an operator in response to a signal from the acoustic sensor indicating that the tissue has undergone a first change in state.

Example 17

The method of Example 16, further comprising: (a) processing a signal from the acoustic sensor to detect a second change in state of the tissue, wherein the state of the tissue changes in response to the energy applied via the end effector; and (b) automatically providing a second notification to an operator in response to a signal from the acoustic sensor indicating that the tissue has undergone a second change in state.

Example 18

A method of operating on tissue, the method comprising: (a) applying a first energy profile to the tissue via an end effector of a surgical instrument; (b) listening to the tissue with an acoustic sensor; (c) processing a signal from the acoustic sensor to detect a first change in state of the tissue, wherein the state of the tissue changes in response to the first energy profile applied via the end effector; (d) automatically transitioning to a second energy profile in response to a signal from the acoustic sensor indicating that the tissue has undergone a first change in state; and (e) applying the second energy profile to the tissue via the end effector.

Example 19

The method of Example 18, further comprising: (a) processing a signal from the acoustic sensor to detect a second change in state of the tissue, wherein the state of the tissue changes in response to the second energy profile applied via the end effector; and (b) automatically ceasing delivery of energy to tissue via the end effector in response to a signal from the acoustic sensor indicating that the tissue has undergone a second change in state.

Example 20

The method of any one or more of Examples 18 through 19, wherein applying the first energy profile to the tissue via the end effector comprises applying ultrasonic energy to the tissue via the end effector, wherein applying the second energy profile to the tissue via the end effector comprises applying RF energy to the tissue via the end effector.

V. Miscellaneous

The foregoing examples have been provided in the context of variations of surgical instrument (12), which is operable to apply ultrasonic and/or RF energy to tissue. However, the teachings herein are not limited to instruments that are operable to apply ultrasonic and/or RF energy to tissue. For instance, the teachings herein may also be readily applied to instruments that are only operable to apply ultrasonic energy to tissue. Merely illustrative examples of such instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. The teachings herein may also be readily applied to instruments that are only operable to apply RF energy to tissue. Merely illustrative examples of such instruments include the ENSEAL® Tissue Sealing Device by Ethicon Endo-Surgery, Inc., of Cincinnati, Ohio. Other suitable kinds of instruments to which the teachings herein may be applied will be apparent to those of ordinary skill in the art in view of the teachings herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

We claim:

1. An apparatus, comprising:
   (a) a body;
   (b) a shaft assembly extending distally from the body, wherein the shaft assembly has a distal end;
   (c) an end effector located at the distal end of the shaft assembly, wherein the end effector is operable to apply at least one of ultrasonic or RF energy to tissue and thereby change a state of the tissue;
   (d) a first acoustic sensor configured to pick up sound emitted by tissue; and
   (e) a processor in communication with the first acoustic sensor, wherein the processor is configured to provide an automated response in response to a signal from the first acoustic sensor indicating a change in the state of the tissue by changing an energy profile associated with the at least one of ultrasonic or RF energy applied to the tissue,
   wherein the processor is configured to provide the automated response in response to the signal from the first acoustic sensor indicating the change in the state of the tissue by changing the energy profile from one of an ultrasonic energy profile or an RF energy profile to the other of the ultrasonic energy profile or the RF energy profile.

2. The apparatus of claim 1, wherein the first acoustic sensor is secured to the distal end of the shaft assembly.

3. The apparatus of claim 1, wherein the first acoustic sensor is secured to the end effector.

4. The apparatus of claim 1, wherein the first acoustic sensor comprises a microphone.

5. The apparatus of claim 1, further comprising a second acoustic sensor.

6. The apparatus of claim 5, wherein the second acoustic sensor is located in the body.

7. The apparatus of claim 5, wherein the processor is further configured to cancel out ambient noise picked up by the second acoustic sensor and thereby filter the signal from the first acoustic sensor.

8. The apparatus of claim 1, further comprising a user feedback feature, wherein the processor is configured to provide an automated notification to an operator via the user feedback feature.

9. The apparatus of claim 8, wherein the user feedback feature is located in or on the body.

10. The apparatus of claim 8, further comprising a generator, wherein the generator is configured to provide power to drive the end effector, wherein the generator is remotely located relative to the body, wherein the user feedback feature is located in or on the generator.

11. The apparatus of claim 8, wherein the processor is configured to provide a first automated notification to an operator via the user feedback feature in response to a signal from the first acoustic sensor indicating a first change in the state of the tissue, wherein the processor is further configured to provide a second automated notification to an operator via the user feedback feature in response to a signal from the first acoustic sensor indicating a second change in the state of the tissue.

12. The apparatus of claim 1, wherein the processor is configured to change an energy profile via the end effector in response to a signal from the first acoustic sensor indicating a first change in the state of the tissue, wherein the processor is further configured to cease delivery of energy to the tissue via the end effector in response to a signal from the first acoustic sensor indicating a second change in the state of the tissue.

13. The apparatus of claim 1, wherein the end effector includes a clamp arm pivotable relative to the shaft assembly.

14. The apparatus of claim 1, wherein the first acoustic sensor is positioned on an exterior of the shaft assembly.

15. A method of operating on tissue, the method comprising:
   (a) applying energy to the tissue via an end effector of a surgical instrument, wherein applying energy to the tissue via the end effector comprises applying at least one of ultrasonic or RF energy to the tissue via the end effector, wherein applying energy to the tissue via an end effector of a surgical instrument includes applying a first energy profile to the tissue;
   (b) listening to the tissue with an acoustic sensor;
   (c) processing a signal from the acoustic sensor to detect a first change in state of the tissue, wherein the state of the tissue changes in response to the energy applied via the end effector;
   (d) automatically providing a first notification to an operator in response to a signal from the acoustic sensor indicating that the tissue has undergone a first change in state, wherein the state of the tissue changes in response to the at least one of ultrasonic or RF energy applied via the end effector;
   (e) automatically transitioning to a second energy profile in response to the signal from the acoustic sensor indicating that the tissue has undergone the first change in state; and
   (f) applying the second energy profile to the tissue via the end effector,
   wherein applying one of the first or second energy profiles to the tissue via the end effector comprises applying ultrasonic energy to the tissue via the end effector, wherein applying the other of the first or second energy profiles to the tissue via the end effector comprises applying RF energy to the tissue via the end effector.

16. The method of claim 15, further comprising:
   (a) processing a signal from the acoustic sensor to detect a second change in state of the tissue, wherein the state of the tissue changes in response to the at least one of ultrasonic or RF energy applied via the end effector; and
   (b) automatically providing a second notification to an operator in response to a signal from the acoustic sensor indicating that the tissue has undergone a second change in state.

17. The method of claim 15, wherein applying ultrasonic energy to the tissue via the end effector cuts the tissue, wherein applying RF energy to the tissue via the end effector seals the tissue.

18. A method of operating on tissue, the method comprising:
  (a) applying a first energy profile to the tissue via an end effector of a surgical instrument;
  (b) listening to the tissue with an acoustic sensor;
  (c) processing a signal from the acoustic sensor to detect a first change in state of the tissue, wherein the state of the tissue changes in response to the first energy profile applied via the end effector;
  (d) automatically transitioning to a second energy profile in response to a signal from the acoustic sensor indicating that the tissue has undergone a first change in state; and
  (e) applying the second energy profile to the tissue via the end effector,
  wherein applying the first energy profile to the tissue via the end effector comprises applying ultrasonic energy to the tissue via the end effector, wherein applying the second energy profile to the tissue via the end effector comprises applying RF energy to the tissue via the end effector.

19. The method of claim 18, further comprising:
  (a) processing a signal from the acoustic sensor to detect a second change in state of the tissue, wherein the state of the tissue changes in response to the second energy profile applied via the end effector; and
  (b) automatically ceasing delivery of energy to tissue via the end effector in response to a signal from the acoustic sensor indicating that the tissue has undergone a second change in state.

20. The method of claim 19, wherein the first change in state of the tissue includes the tissue transitioning to a cut state, wherein the second change in state of the tissue includes the tissue transitioning to a sealed state.

* * * * *